US011514688B2

(12) United States Patent
Cronje et al.

(10) Patent No.: US 11,514,688 B2
(45) Date of Patent: Nov. 29, 2022

(54) DROWSINESS DETECTION SYSTEM (71) Applicant: 5DT, Inc., Orlando, FL (US)

(72) Inventors: Jaco Cronje, Zwavelpoort (SA); Johann Ephraim Hough, Brooklyn (SA)

(73) Assignee: 5DT, Inc., Orlando, FL (US)

( * ) Notice: Subject to any disclaimer, the term of this patent is extended or adjusted under 35 U.S.C. 154(b) by 0 days.

(21) Appl. No.: 17/055,991

(22) PCT Filed: Oct. 22, 2019

(86) PCT No.: PCT/IB2019/058990
§ 371 (c)(1),
(2) Date: Nov. 16, 2020

(87) PCT Pub. No.: WO2020/084469
PCT Pub. Date: Apr. 30, 2020

(65) Prior Publication Data
US 2021/0241011 A1 Aug. 5, 2021

Related U.S. Application Data (60) Provisional application No. 62/748,596, filed on Oct. 22, 2018.

(51) Int. Cl.
*G06V 20/59* (2022.01)
*G06T 7/70* (2017.01)
(Continued)

(52) U.S. Cl.
CPC .......... *G06V 20/597* (2022.01); *A61B 5/1103* (2013.01); *A61B 5/1114* (2013.01);
(Continued)

(58) Field of Classification Search
CPC .......... G06K 9/00845; G06K 9/00281; G06K 9/00335; G06K 9/00228; A61B 5/163;
(Continued)

(56) References Cited

U.S. PATENT DOCUMENTS

2010/0238034 A1    9/2010 Gunaratne
2014/0139655 A1    5/2014 Mirar
(Continued)

FOREIGN PATENT DOCUMENTS

CN    108309311 A    7/2018

OTHER PUBLICATIONS

Australian Transport Council, National Road Safety Strategy, 2011-2020, May 2011, pp. 1-122.
Drunk driving law by country, Wikipedia, Mar. 11, 2020, pp. 1-19.
Babaeian, et al,. Real Time Driver Drowsiness Detection Using a Logistic-Regression-Based Machine Learning Algorithm, Department of Electrical Engineering, California State University, Long Beach, 2016, IEEE Green Energy and Systems Conference (IGSEC) Nov. 2016, pp. 1-6.
(Continued)

*Primary Examiner* — John B Strege
(74) *Attorney, Agent, or Firm* — Greenberg Traurig, LLP (57) ABSTRACT

A machine-implemented method for automated detection of drowsiness, which includes receiving from an imaging device directed at the face of an operator a series of images of the face of the operator onto processing hardware, on the processor detecting facial landmarks of the operator from the series of images to determine the level of talking by the operator, the level of yawning of the operator, the PERCLOS of the operator, on the processor detecting the facial pose of the operator from the series of images to determine the level of gaze fixation by the operator, on the processor calculating the level of drowsiness of the operator by ensembling the level of talking by the operator, the level of yawning of the operator, the PERCLOS of the operator and the level of gaze fixation by the operator, and generating an alarm when the calculated level of drowsiness of the operator exceeds a predefined value.

7 Claims, 3 Drawing Sheets

Block Diagram of the Drowsiness Detection Method (51) Int. Cl.
   *A61B 5/16* (2006.01)
   *A61B 5/11* (2006.01)
   *A61B 5/18* (2006.01)
   *A61B 5/00* (2006.01)
   *B60Q 9/00* (2006.01)
   *G06T 7/20* (2017.01)
   *G08B 21/06* (2006.01)
   *G06V 40/20* (2022.01)
   *G06V 40/16* (2022.01)

(52) U.S. Cl.
   CPC .......... *A61B 5/1123* (2013.01); *A61B 5/1128* (2013.01); *A61B 5/163* (2017.08); *A61B 5/165* (2013.01); *A61B 5/18* (2013.01); *A61B 5/6893* (2013.01); *A61B 5/7267* (2013.01); *B60Q 9/00* (2013.01); *G06T 7/20* (2013.01); *G06T 7/70* (2017.01); *G06V 40/161* (2022.01); *G06V 40/171* (2022.01); *G06V 40/20* (2022.01); *G08B 21/06* (2013.01); *A61B 2560/0247* (2013.01); *G06T 2207/30201* (2013.01); *G06T 2207/30268* (2013.01)

(58) Field of Classification Search
   CPC ....... A61B 5/7267; A61B 5/18; A61B 5/1128; A61B 5/6893; A61B 5/1103; A61B 5/1123; A61B 5/1114; A61B 5/165; A61B 2560/0247; G06T 7/20; B60Q 9/00; G08B 21/06
   See application file for complete search history.

(56) References Cited

U.S. PATENT DOCUMENTS

| | | | |
|---|---|---|---|
| 2015/0314681 A1* | 11/2015 | Riley, Sr. | G08B 21/06 340/576 |
| 2016/0185354 A1* | 6/2016 | Lisseman | H04N 5/2252 701/36 |
| 2019/0038204 A1* | 2/2019 | Beck | A61B 5/18 |
| 2019/0213429 A1* | 7/2019 | Sicconi | G06F 3/016 |
| 2021/0129748 A1* | 5/2021 | Tamrakar | A61B 5/1128 |

OTHER PUBLICATIONS

Akrout, et al., Yawning detection by the analysis of variational descriptor form monitoring driver drowsiness, IEEE IPAS's16: International Image Processing Applications and System Conference, Nov. 2016, pp. 1-5.

Zhenhai, et al., Driver Drowsiness Detection Based on Time Series Analysis of Steering Wheel Angular Velocity, State Key Laboratory of Automobile Simulation and Control Jilin University, Changchum, China; 2017 9th International Conference on Measuring Technology Mechatronics Automation; Jan. 2017, pp. 1-3.

Bergasa, et al., Real-Time System for Monitoring Driver Vigilance, IEEE Transactions on Intelligent Transportation Systems, vol. 7, pp. 63-77, No. 1, Jan. 2006.

International Search Report from related PCT application No. PCT/IB19/058990, dated Feb. 12, 2020; 2 pgs.

Written Opinion from related PCT application No. PCT/IB19/058990, dated Feb. 12, 2020; 6 pgs.

* cited by examiner

Figure 1: Block Diagram of the Drowsiness Detection Method

Figure 2: Facial Landmarks that are Detected

Figure 3: Block Diagram of the System

DROWSINESS DETECTION SYSTEM

CROSS-REFERENCE TO RELATED APPLICATION INFORMATION

The present application is a U.S. national stage patent application, pursuant to 35 U.S.C. § 371, of PCT International Application No.: PCT/IB2019/058990, filed Oct. 22, 2019, published as WO2020/084469A1, which claims priority to U.S. provisional patent application No. 62/748,596, filed Oct. 22, 2018, the contents of all of which are hereby incorporated by reference in their entirety.

TECHNICAL FIELD

This invention relates to a drowsiness detection system and a machine-implemented method for automated detection of drowsiness.

BACKGROUND

According to the Australian Transport Council, drowsy driving causes between 20% and 30% of all deaths and injuries on the road [1]. Studies have shown that driving without sleep for 17 hours is comparable to driving with a blood alcohol concentration (BAC) of 0.05 (the legal limit of most countries including the USA, England and South Africa ranges between 0.05% and 0.08% [2]) and driving without sleep for 21 hours is comparable to a BAC of 0.15 (far over the legal limit) [1]. Drowsiness also affects many other industries where vigilance is required and can even be problematic for office workers.

In order to solve this problem, accurate drowsiness detection is needed. This would allow systems to be developed that alert operators when drowsiness is detected. Furthermore, it would allow companies and governments to monitor their operators and enforce vigilance.

Drowsiness detection has received an abundance of attention in recent years from both automotive companies and universities. A variety of approaches and methods have been researched and tested. These methods can be classified into three groups, namely, physiological methods, vehicle movement methods and computer vision methods.

Early methods made use of physiological measures such as respiration rate, heart rate and brain activity [3]. These methods are, however, intrusive as measurement devices must be attached to the operator. This can be dangerous if the measurement devices restrict the movement of the operator. Furthermore, the devices often hinder the comfort of operators and cause distractions, increasing the risk of an incident or accident.

Another method of drowsiness detection, geared towards drivers, is the monitoring of steering wheel movement [4] and vehicle movement. Sensors are typically placed inside the steering wheel or dashboard of a vehicle and measure the angular velocity and acceleration. This data is then used to classify erratic driving and swerving that is a characteristic of drowsy driving. A major drawback of this method is the large impact that road conditions and vehicle speed have on it. If road conditions are bad, drivers may swerve to avoid potholes and other obstacles which could be misinterpreted as drowsy driving. Additionally, the nature of the recorded data requires an extended period of analysis before an accurate classification of drowsiness can be made. This reduces the effectivity of the system as an accident may occur before classification. Placement of the sensors may also be problematic as they may interfere with the driver if they are not built into the vehicle.

Advances in computer vision have allowed drowsiness detection to be performed by observing facial features such as the eyes and mouth. Facial characteristics of drowsiness include a smaller degree of eyelid opening, slow eyelid movement, increased number of blinks, yawning, nodding and gazing. Using an imaging device pointing towards the operator, machine learning and computer vision can be used to detect these characteristics and perform drowsiness detection. This method benefits from the fact that it is non-intrusive and is not affected by road conditions or driving speed when it is performed on drivers.

In one study [5], a system was developed that monitors drowsiness through yawn detection. This method proved successful but resulted in false alarms in cases where operators were tired but not drowsy. Another problem was that operators often covered their mouths while yawning, obstructing the view of the camera. Another study [6] was performed where multiple features were calculated from the faces of drowsy operators in order to determine which features result in the best drowsiness classification. The accuracy of the calculated features is shown below. It is clear that fixed gaze and percentage of eye closure over time (PERCLOS) are the best features for drowsiness detection with an accuracy of 95.6% and 93.1% respectively.

Fixed Gaze: Accuracy: 95.6%
  PERCLOS: Accuracy: 93.1%
  Eye Closure Duration: Accuracy: 84.4%
  Blink Frequency: Accuracy: 80%
  Nodding Frequency: Accuracy: 72.5%

The inventor identified a need to integrate and improve the methods and systems to detect drowsiness with improved accuracy and to take immediate action upon detecting drowsiness of an operator thereby to reduce accidents related to drowsiness of an operator.

RELATED PUBLICATIONS

*Real time driver drowsiness detection using a logistic-regression-based machine learning algorithm* (Babaeian, Bhardwaj, Esquivel, & Mozumdar, 2016) detects drowsiness by computing heart rate variation and using logistic regression based machine learning algorithms.

*Driver Drowsiness Detection Based on Time Series Analysis of Steering Wheel Angular Velocity* (Zhenhai, DinhDat, Hongyu, Ziwen, & Xinyu, 2017) uses a sliding window approach to analyze steering wheel angular velocity and detect a state of drowsiness.

*Yawning detection by the analysis of variational descriptor for monitoring driver drowsiness* (Akrout & Mandi, 2016) performs drowsiness detection by detecting yawning. Yawning is detected by using the Viola-Jones method to detect the mouth and localizing the external lips contour with the method of active contours.

*Real-time system for monitoring driver vigilance* (Bergasa, Nuevo, Sotelo, Barea, & Lopez, 2006) uses the features shown in section 1.0 to calculate drowsiness. They do not use convolutional neural networks (CNNs) to detect faces or landmarks.

SUMMARY OF THE DISCLOSURE

According to a first aspect of the invention, there is provided a drowsiness detection system, which includes:
  an image sensor, directed towards a face of an operator for capturing a series of images of a face of the operator;

at least one movement sensor installed in a vehicle to monitor movement of the vehicle;

processing hardware which comprises a central processing unit, a data storage facility in communication with the central processing unit and input/output interfaces in communication with the central processing unit, the processing hardware being configured to implement a set of trained convolution neural networks (CNNs) comprising:

a face detection group into which at least one image of the series of images is received from the image sensor for detecting the face of the operator in the at least one image;

a face tracking group which match the face in the at least one image in the series of images with the same face in a previous image in the series of images and which then track the motion of the same face in the further series of images;

a facial landmark detection group which detects movement of a plurality of facial landmarks in the further series of images, the facial landmarks selected from the group of jawline, eyebrows, eyelids, nose, pupils and lips;

a face pose detection group which determine the orientation of the face of the operator; and a drowsiness detection group which includes any one or more of:

a yawning and talking detection group, which is trained to determine whether an operator is talking, thereby to provide an indication of alertness, and whether an operator is yawning, thereby to provide an indication of drowsiness;

a PERCLOS (percentage of eye closure over time) calculation, which determines the percentage of eye closure over a period of time, thereby to provide an indication of drowsiness if the PERCLOS exceeds a predefined value;

a fixed gaze calculation, which determines when an operator's gaze time exceeds a predefined value, thereby to provide an indication of drowsiness; and an erratic movement detection group, which is trained to determine when a vehicle's movement resembles that of a drowsy driver, thereby to provide an indication of drowsiness.

The drowsiness detection group may include an ensemble function, which ensembles outputs from any one or more of the yawning and talking detection group, the PERCLOS calculation, the fixed gaze calculation, and the erratic movement detection group thereby to generate an alarm when the ensembled value exceeds a predefined value for a drowsy operator.

The drowsiness detection group may include a drowsiness ensemble calculation which calculates the level of drowsiness of an operator by any one of:

predefined algorithms that calculate a numerical value representative of the drowsiness of the operator by using mathematical equations and conditional statements applied to the outputs from the yawning and talking detection group, the PERCLOS detection group, the fixed gaze detection group and the erratic movement detection group; and a machine learning algorithm trained with outputs from the yawning and talking detection group, the PERCLOS detection group, the fixed gaze detection group and the erratic movement detection group to determine a level of drowsiness of an operator.

The ensemble algorithm may include machine learning algorithms such as neural networks, regression tree ensembles, linear regression and polynomial regression.

The drowsiness detection system may include an ambient light sensor, installed in proximity to the operator, in use to measure ambient light in the environment of the operator to aid the machine learning and computer vision algorithms.

According to another aspect of the invention, there is provided a machine-implemented method for automated detection of drowsiness, which includes:

receiving onto processing hardware a series of images of an operator, processing the series of images of the operator on processing hardware by a set of trained convolution neural networks comprising:

a face detection group into which at least one image of the series of images is received from the image sensor for detecting the face of the operator in the at least one image;

a face tracking group which match the face in the at least one image in the series of images with the same face in a previous image in the series of images and which then track the motion of the same face in the further series of images;

a facial landmark detection group which detects movement of a plurality of facial landmarks in the further series of images, the facial landmarks selected from the group of jawline, eyebrows, eyelids, nose, pupils and lips;

a face pose detection group which determine the orientation of the face of the operator; and a drowsiness detection group, which includes any one or more of:

a yawning and talking detection group, which is trained to determine whether an operator is talking, thereby to provide an indication of alertness, and whether an operator is yawning, thereby to provide an indication of drowsiness;

a PERCLOS (percentage of eye closure over time) calculation, which determines the percentage of eye closure over a period of time, thereby to provide an indication of drowsiness if the PERCLOS exceeds a predefined value;

a fixed gaze calculation, which determines when an operator's gaze time exceeds a predefined value, thereby to provide an indication of drowsiness;

an erratic movement detection group, which is trained to determine when a vehicle movement exceeds a predefined value, thereby to provide an indication of drowsiness;

ensembling the outputs received from any one or more of the yawning and talking detection group, the PERCLOS calculation, the a fixed gaze calculation, and the erratic movement detection group thereby to generate an alarm when the ensembled value exceed a predefined value for a drowsy operator; and generating an alarm when the level of drowsiness of the operator determined by the processing hardware exceeds a predefined value.

According to yet another aspect of the invention, there is provided a machine-implemented method for automated detection of drowsiness, which includes:

receiving from an imaging device directed at the face of an operator a series of images of the face of the operator onto processing hardware;

on the processor detecting facial landmarks of the operator from the series of images to determine the level of talking by the operator, the level of yawning of the operator, the PERCLOS of the operator;

on the processor detecting the facial pose of the operator from the series of images to determine the level of gaze fixation by the operator;

on the processor calculating the level of drowsiness of the operator by ensembling the level of talking by the operator, the level of yawning of the operator, the PERCLOS of the operator and the level of gaze fixation by the operator; and generating an alarm when the calculated level of drowsiness of the operator exceeds a predefined value.

The step of detecting facial landmarks of the face of the operator includes the prior steps of:

detecting a face of the operator in the series of images; and tracking the face of the operator in the series of images.

The step of detecting facial landmarks of the face of the operator includes detecting any one or more of:

movement of the jawline of the operator in the series of images;

movement of the eyebrows of the operator in the series of images;

movement of the eyelids of the operator in the series of images;

movement of the nose of the operator in the series of images;

movement of the pupils of the operator in the series of images; and movement of the lips of the operator in the series of images.

The level of gaze fixation of an operator may be detected by calculating the variance of the operator's head orientation and the operator's pupil movement, the variance of both the head's orientation and pupil movement being used to predict the drowsiness level of the operator. For example, an operator of a vehicle would normally be checking the rear-view mirrors and side-view mirrors, blind spots and scanning the road ahead. As the drowsiness level of an operator increases, their gaze becomes fixated on a single area. The movement of their head and pupils, therefore, decrease significantly.

The invention is now described, by way of non-limiting example, with reference to the accompanying drawings.

DETAILED DESCRIPTION

The drowsiness detection method makes use of multiple sensors, processes and algorithms that work together to output an accurate drowsiness level. An overview of the system is given in FIG. 1. The system starts by obtaining data from the sensors (110). The visual data is then passed to machine learning and computer vision algorithms (120) to be further processed. The processed data and data obtained from other sensors are then passed to the second set of algorithms (130) that determine the level of drowsiness (139).

Figure 1:
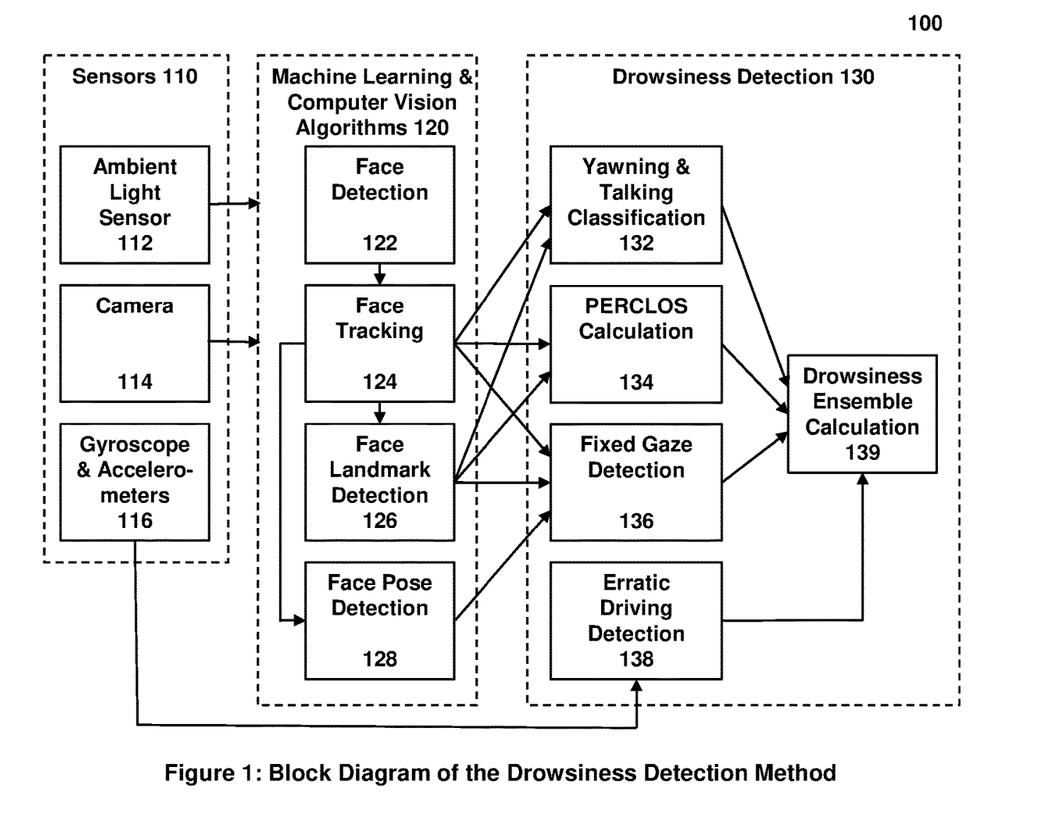
FIG. 1 shows a block diagram of a machine-implemented method for automated detection of drowsiness in accordance with one aspect of the invention.

1. Sensors (110)

As shown in FIG. 1, the system makes use of several sensors (112, 114 and 116) to provide data to the algorithms. The sensors used include but are not limited to ambient light sensors (112), imaging devices such as cameras (114) and gyroscopes and accelerometers (116).

The camera (114) may be placed anywhere provided that the face of the operator is in view of the camera. A position that allows both eyes of the operator to be seen is beneficial since the method monitors the eyes to determine drowsiness. The system does not rely on the type of camera used as long as it provides a clear image of the driver's face. This means that the camera should have adequate resolution and should implement a form of night vision if the system is required to operate at night.

The ambient light sensor (112) should be placed close to the operator in order to detect the amount of light in the environment.

The gyroscope (116) is attached to the steering wheel of the vehicle and measures the angular velocity of the steering wheel. The accelerometers (116) are placed at a fixed location on or in the vehicle and measures the sway (left/right sideways movement) of the vehicle. Either the gyroscope or the accelerometers (116), or both the gyroscope and the accelerometer, may be used to detect erratic driving.

2. Machine Learning and Computer Vision Algorithms (120)

The machine learning and computer vision algorithms (120) receive visual data from the camera (114) in the form of frames. They perform processing on the frames in order to interpret their contents and output numeric data that can easily be used by other algorithms. These algorithms make use of machine learning and CNNs to learn how to interpret visual data. This is done in several steps. First, a large set of data must be collected on which the algorithm can train. Next, each image in the dataset needs to be labelled with the desired output of the network. The network is then trained by supplying the image as an input and comparing the output of the network with the desired output for the image. If the output of the network matches the desired output, the network does not need to update itself. If the output differs, the network calculates an error and uses gradient descent to update the weights of the network to minimize the error. In this manner, the network learns how to provide the desired output from an input image.

The first algorithm that is run is face detection (122). It takes an image as an input and outputs bounding boxes for all the faces detected in the image. Once all of the faces have been detected, a face tracking algorithm (124) is run. This uses the detected faces and tries to match them to the faces seen in the previous frame. It does this by performing face recognition on the faces and by tracking their motion.

Figure 2:
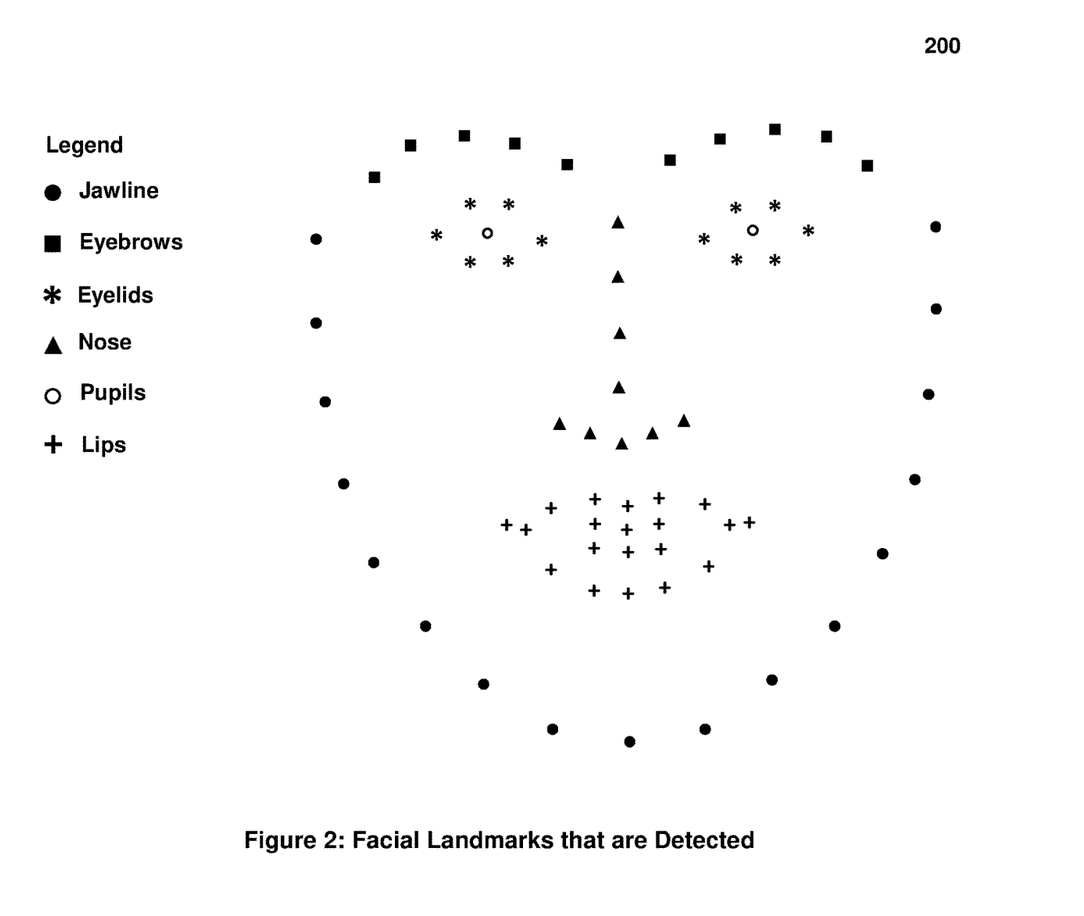
FIG. 2 shows a diagram of the facial landmarks that are detected in the method of FIG. 1.

Next, it performs facial landmark detection (126) on the detected faces. This once again takes the captured image as the input and outputs the points on the face which it has been trained to detect. The network can be trained to detect points anywhere on the face. Since the goal is to monitor the eyes and mouth, the network is trained to detect landmarks primarily on the lips, eyelids and pupils of the face. FIG. 2 shows the facial landmarks that are detected.

Lastly, a face pose detection network (128) is used to determine the orientation of the detected faces. The network takes a cropped face as the input and outputs the orientation of the face.

As shown in FIG. 1, the machine learning algorithms also make use of an ambient light sensor (112). This allows the algorithms to automatically adjust to the light conditions within the observed space, such as but not limited to a cabin.

3. Drowsiness Detection Algorithms (130)

Several algorithms are implemented to calculate features that accurately classify drowsiness. Their outputs are then ensembled (combined) to determine whether the operator is drowsy.

The first algorithm determines whether the operator is yawning or talking (132). Talking indicates that the operator is awake and mentally stimulated and therefore reduces the level of drowsiness. On the other hand, yawning indicates that the operator is getting tired and that drowsiness may be present. The system detects both talking and yawning by using the output of the facial landmark detection algorithm (126). It monitors the distance between the points on the top and the bottom lips of the operator. Talking is classified when the distance between the lips change rapidly for a period of time. Yawning is classified when the distance increases and passed the normal open size of the mouth, then remains open for a period of time and then closes again.

The second algorithm (PERCLOS) (134) monitors the eyelids of the operator by analyzing the output of the facial landmark detection algorithm (126). It starts by creating a baseline for the operator's eyes by determining the nominal size of the operator's eyes when they are open and closed. It then uses this baseline to calculate the percentage of eye closure on each frame. The average percentage of eye closure (PERCLOS) is then calculated over two periods of time lasting two seconds and thirty seconds respectively. Since PERCLOS calculates the average eye closure over time, it inherently measures all of the characteristics that indicate drowsiness, namely, a smaller degree of eyelid opening, slow eyelid movement, and an increased number of blinks. Furthermore, since it is calculated over both a short and long period of time, it is able to detect instantaneous changes in drowsiness such as closing of the eyes for an extended period of time and long-lasting changes such as slowed blinking or a smaller degree of eye-opening.

The third algorithm performs fixed gaze detection (136) by monitoring the pupils and the face pose (128). A vigilant operator is generally expected to look around often. In the case of a driver, he/she should be checking the rear-view mirrors and side-view mirrors, blind spots and scanning the road ahead. As the drowsiness level of an operator increases, their gaze becomes fixated on a single area. The movement of their head and pupils, therefore, decrease significantly. The algorithm detects this by calculating the variance of the head's orientation and the pupil movement. The variance of both features is then used to predict the drowsiness level of the driver in the final algorithm. If the function that the operator performs requires him/her to fix their gaze, this feature will not be calculated.

Lastly, a specialized algorithm is implemented that detects drowsiness in drivers by detecting erratic driving (138) by monitoring the angular velocity of the steering wheel (138) and/or the sway (left/right sideways movement) of the vehicle. When drivers get drowsy they tend to drift out of their lane. When they realize that they have been drifting they swerve back into their lane. This algorithm identifies the erratic driving behavior by looking for short spikes in the angular velocity and/or acceleration and classifies it as drowsiness. If the operator being monitored is not a driver, this feature will not be calculated.

The final algorithm (139) receives the drowsiness features output by the previous algorithms as inputs. It can then calculate the final drowsiness level of the operator in two ways.

The first is by using equations or conditional statements that takes all the features into account and outputs the level of drowsiness. For example, an equation can be implemented that simply weighs the outputs of all the features and outputs a percentage of drowsiness. Conditional statements can be added to improve performance, for instance, if the PERCLOS outputs for example 0.5 but the fixed gaze outputs for example 0.1, the drowsiness output can be capped to for example 0.1 since the operator is vigilant and looking around.

The second method makes use of machine learning algorithms. These algorithms take the drowsiness features as inputs and are trained with many examples of operators at different stages of drowsiness. It then learns the relationship between the features and the drowsiness level of the operator. Any machine learning algorithm or combination of algorithms may be used, this includes but is not limited to neural networks, regression tree ensembles, linear regression and polynomial regression.

Figure 3:
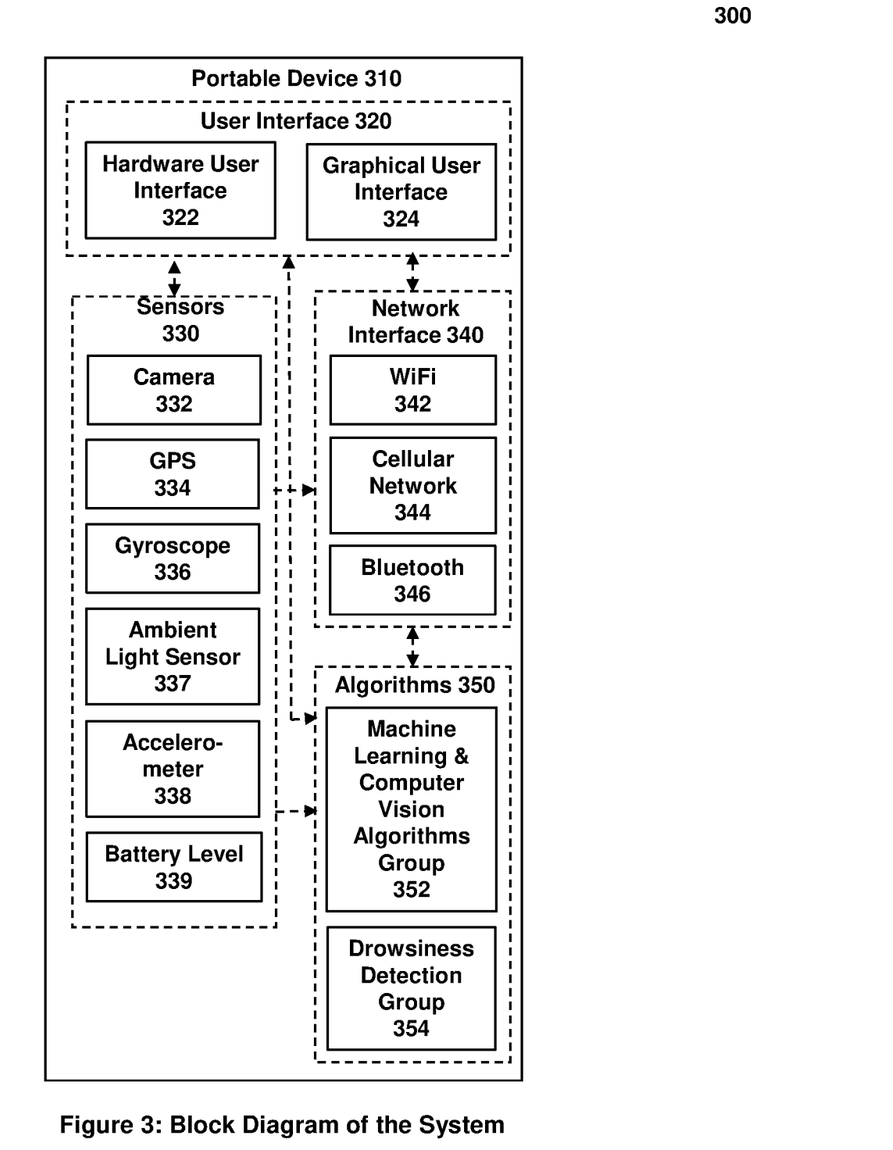
FIG. 3 shows a block diagram of a drowsiness detection system in accordance with another aspect of the invention.

4. Hardware Implementation of the System
4.1 Portable Device (310)

The portable device gathers data from sensors (330) and runs algorithms (350), such as, but not limited to, machine learning and computer vision algorithms (352) and drowsiness detection algorithms (354) on the collected data.

The device interfaces with multiple sensors that may be built into the device or connected to it externally using either a wired or wireless connection. The type and number of sensors used will vary depending on the nature of the algorithms that are running.

The sensors that may be used include, but are not limited to, cameras (332) (visible and infrared (IR)), global positioning system (GPS) (334), ambient light sensors (337), accelerometers (338), gyroscopes (336) and battery level sensors (339). The sensors may either send raw or processed data to the algorithms to be analysed.

Various algorithms (350) may be used to process and interpret the sensor data. The algorithms (350) may use data obtained directly from the sensors (330) and data obtained from the server (not shown). The algorithms (356) include a machine learning and computer vision algorithm group (352) and a drowsiness detection group (354).

The portable device (310) is provided with a network interface (340) comprising of a Wi-Fi interface (342), a cellular network interface (GSM, HSPA, LTE) (344) and a Bluetooth interface (346) to communicate with remote systems (not shown).

The portable device may also include a user interface (UI) (320) that may consist of a hardware user interface (HUI) (322) and/or a graphical user interface (GUI) (324). The UI can be used to log in to the system, control it and view information collected by it.

This system implements drowsiness detection by improving on existing methods in two ways.

Firstly, it makes use of advanced machine learning and computer vision algorithms to process a video stream and accurately extracts data from it in real-time. This is done by training convolutional neural networks (CNNs) that take an image as an input and output the desired data.

Secondly, it uses the outputs of the machine learning and computer vision algorithms to calculate several features that have been proven to accurately classify drowsiness. These include PERCLOS, fixed gaze, yawning, talking and erratic driving detection when applied to drivers. An ensemble (combination) of these features is taken, together with data from other sensors, in order to accurately determine the drowsiness level of the operator.

The inventor is of the opinion that the invention as described provides a new and improved drowsiness detection system and a machine-implemented method for automated detection of drowsiness.

REFERENCES

[1] Australian Transport Council, "National Road Safety Strategy 2011-2020," 2011.
[2] Wikipedia, "Drunk driving law by country," [Online]. Available: https://en.wikipedia.org/wiki/Drunk_driving_law_by_country.
[3] M. Babaeian, N. Bhardwaj, B. Esquivel and M. Mozumdar, "Real time driver drowsiness detection using a logistic-regression-based machine learning algorithm," 2016 *IEEE Green Energy and Systems Conference (IGSEC)*, pp. 1-6, November 2016.

[4] G. Zhenhai, L. DinhDat, H. Hongyu, Y. Ziwen and W. Xinyu, "Driver Drowsiness Detection Based on Time Series Analysis of Steering Wheel Angular Velocity," 2017 *9th International Conference on Measuring Technology and Mechatronics Automation (ICMTMA)*, pp. 99-101, 2017.

[5] B. Akrout and W. Mandi, "Yawning detection by the analysis of variational descriptor for monitoring driver drowsiness," 2016 *International Image Processing, Applications and Systems (IPAS)*, pp. 1-5, 2016.

[6] L. M. Bergasa, J. Nuevo, M. A. Sotelo, R. Barea and M. E. Lopez, "Real-time system for monitoring driver vigilance," *IEEE Transactions on Intelligent Transportation Systems*, pp. 63-77, 2006.

The invention claimed is:

1. A drowsiness detection system comprising:
    an image sensor, directed towards a face of a driver for capturing a series of images of a face of the driver;
    at least one movement sensor installed in a vehicle to monitor erratic movement of the vehicle;
    processing hardware which comprises a central processing unit, a data storage facility in communication with the central processing unit and input/output interfaces in communication with the central processing unit, the processing hardware being configured to implement a set of trained convolution neural networks (CNNs) comprising:
        a face detection group into which at least one image of the series of images is received from the image sensor for detecting the face of the driver in the at least one image;
        a face tracking group which match the face in the at least one image in the series of images with the same face in a previous image in the series of images and which then track the motion of the same face in the further series of images;
        a facial landmark detection group which detects movement of a plurality of facial landmarks in the further series of images, the facial landmarks selected from the group of jawline, eyebrows, eyelids, nose, pupils and lips;
        a face pose detection group which determine the orientation of the face of the driver; and
        a drowsiness detection group which includes all of:
            a yawning and talking detection group, which is trained to determine whether the driver is talking, thereby to provide an indication of alertness, and whether the driver is yawning, thereby to provide an indication of drowsiness;
            a PERCLOS (percentage of eye closure over time) calculation, which determines the percentage of eye closure over a period of time, thereby to provide an indication of drowsiness if the PERCLOS exceeds a predefined value;
            a fixed gaze calculation, which determines when the driver's gaze time exceeds a predefined value, thereby to provide an indication of drowsiness; and
        an erratic movement detection group, which is trained to determine when a vehicle movement exceeds a predefined value, thereby to provide an indication of drowsiness.

2. The drowsiness detection system of claim 1, wherein the drowsiness detection group includes the erratic movement detection group and an ensemble algorithm, which ensembles outputs from the erratic movement detection group that detects erratic movement of the vehicle, and any one or more of the yawning and talking detection group, the PERCLOS calculation, the fixed gaze calculation to determine the drowsiness of the driver.

3. The drowsiness detection system of claim 2, wherein the ensemble algorithm calculates the level of drowsiness of the driver by the erratic movement detection group, which detects erratic movement of the vehicle, and
    all of predefined algorithms that calculate a numerical value representative of the drowsiness of the driver by using mathematical equations and conditional statements applied to the outputs from the yawning and talking detection group, the PERCLOS detection group, and/or the fixed gaze detection group; and
    a machine learning algorithm trained with outputs from the yawning and talking detection group, the PERCLOS detection group, the fixed gaze detection group and the erratic movement detection group to determine a level of drowsiness of the driver.

4. The drowsiness detection system of claim 3, wherein the ensemble algorithm includes a machine learning algorithm comprising a neural networks.

5. A machine-implemented method for automated detection of drowsiness, the method comprising:
    receiving onto processing hardware a series of images of the driver,
    processing the series of images of the driver on processing hardware by a set of trained convolution neural networks comprising:
        a face detection group into which at least one image of the series of images is received from the image sensor for detecting the face of the driver in the at least one image;
        a face tracking group which match the face in the at least one image in the series of images with the same face in a previous image in the series of images and which then track the motion of the same face in the further series of images;
        a facial landmark detection group which detects movement of a plurality of facial landmarks in the further series of images, the facial landmarks selected from the group of jawline, eyebrows, eyelids, nose, pupils and lips;
        a face pose detection group which determine the orientation of the face of the driver; and
        a drowsiness detection group, which includes all of:
            a yawning and talking detection group, which is trained to determine whether the driver is talking, thereby to provide an indication of alertness, and whether the driver is yawning, thereby to provide an indication of drowsiness;
            a PERCLOS (percentage of eye closure over time) calculation, which determines the percentage of eye closure over a period of time, thereby to provide an indication of drowsiness if the PERCLOS exceeds a predefined value;
            a fixed gaze calculation, which determines when the driver's gaze time exceeds a predefined value, thereby to provide an indication of drowsiness; and
            an erratic movement detection group, which is trained to determine when a vehicle's movement resembles that of a drowsy driver, thereby to provide an indication of drowsiness;
    ensembling the outputs received from all of the yawning and talking detection group, the PERCLOS calculation, the a fixed gaze calculation, and the erratic movement detection group thereby to generate an alarm when the ensembled value exceed a predefined value for a drowsy driver; and generating an alarm when the level of drowsiness of the driver determined by the processing hardware exceeds a predefined value.

6. The drowsiness detection system of claim 3, wherein the ensemble algorithm includes machine learning algorithms selected from one or more of a regression tree ensemble, linear regression, and/or polynomial regression.

7. A drowsiness detection system comprising:

an image sensor, directed towards a face of a driver of a vehicle and configured to capture a series of images of the face of the driver;

at least one movement sensor installed in the vehicle to monitor erratic movement of the vehicle, driven by the driver;

processing hardware which comprises a central processing unit, a data storage facility in communication with the central processing unit and input/output interfaces in communication with the central processing unit, wherein the processing hardware is configured to implement a drowsiness detection algorithm which includes:

an erratic movement detection group, which is trained to determine when a vehicle movement exceeds a predefined value, and thereby to provide an indication of erratic vehicle movement; and all of:

a yawning and talking detection group, which is trained to determine whether a driver is talking, thereby to provide an indication of alertness, and whether a driver is yawning, thereby to provide an indication of drowsiness based on a series of images taken of the face of the driver;

a PERCLOS (percentage of eye closure over time) calculation, which determines the percentage of eye closure over a period of time, thereby to provide an indication of drowsiness if the PERCLOS exceeds a predefined value based on a series of images taken of the face of the driver; and/or a fixed gaze calculation, which determines when a driver's gaze time exceeds a predefined value, thereby to provide an indication of drowsiness based on a series of images taken of the face of the driver.

* * * * *